United States Patent [19]

Bank

[11] Patent Number: 5,312,945
[45] Date of Patent: May 17, 1994

[54] PROCESS FOR PREPARATION OF β-CYANOALKYLSILANES USING RUTHENIUM CATALYST

[75] Inventor: Howard M. Bank, Freeland, Mich.

[73] Assignee: Dow Corning Corporation, Midland, Mich.

[21] Appl. No.: 38,313

[22] Filed: Mar. 29, 1993

[51] Int. Cl.$^5$ ............................................. C07F 7/10
[52] U.S. Cl. ............................................. 556/415
[58] Field of Search ................................. 556/415

[56] References Cited

U.S. PATENT DOCUMENTS

| | | | |
|---|---|---|---|
| 2,860,153 | 11/1958 | Saam | 556/415 |
| 2,906,764 | 9/1959 | Jex et al. | 556/415 |
| 2,907,784 | 10/1959 | Jex et al. | 556/415 |
| 2,971,970 | 2/1961 | Bluestein | 556/415 |
| 5,103,033 | 4/1992 | Bank | 556/415 |
| 5,126,468 | 6/1992 | Bank | 556/415 |
| 5,126,469 | 6/1992 | Bank | 556/415 |

OTHER PUBLICATIONS

Rajkumar et al., Organometallics 8:549 (1989).

*Primary Examiner*—Paul F. Shaver
*Attorney, Agent, or Firm*—William F. Boley

[57] ABSTRACT

The present invention is a process for the preparation of hydrolyzable β-cyanoalkylsilanes. More particularly, this invention relates to the catalytic addition of organohydrosilane to α,β-unsaturated olefinic nitriles to form B-cyanoalkylsilanes. The present process employs a catalyst comprising a ruthenium compound. The preferred catalyst for the present process is a ruthenium compound having at least one tertiary phosphine ligand. The process is conducted at a temperature within a range of about 50° C. to 300° C.

18 Claims, No Drawings

PROCESS FOR PREPARATION OF β-CYANOALKYLSILANES USING RUTHENIUM CATALYST

BACKGROUND OF INVENTION

The present invention is a process for the preparation of hydrolyzable β-cyanoalkylsilanes. More particularly, this invention relates to the catalytic addition of organohydrosilanes to α,β-unsaturated olefinic nitriles to form β-cyanoalkylsilanes. The present process employs a catalyst comprising a ruthenium compound. The preferred catalyst for the present process is a ruthenium compound having at least one tertiary phosphine ligand.

Beta-cyanoalkylsilanes having hydrolyzable chlorines bonded to the silicon atom are useful for the production of polyorganosiloxanes containing the β-cyanoalkyl substituent. The silicon-bonded β-cyanoalkyl substituent is extremely resistant to hydrolysis and cleavage under hot, humid conditions and imparts these characteristics to the polyorganosiloxane of which they are a substituent. The presence of the silicon bonded β-cyanoalkyl substituent on polyorganosiloxanes also tends to stabilize the polyorganosiloxanes against swelling induced by liquid hydrocarbons. In addition, β-cyanoalkylsilanes having hydrolyzable chlorines are useful reactive intermediates for forming, for example, gamma-aminoorganotrialkoxysilanes which are useful as surface treating agents.

A number of catalyst have been reported useful in the preparation of β-cyanoalkylsilanes. Saam, U.S. Pat. No. 2,860,153, issued Nov. 11, 1958, describe a process for preparing β-cyanoethyltrichlorosilane by heating at a temperature less than 150° C. a mixture of acrylonitrile and organohydrosilane with a catalytic amount of an amine.

Jex et al., U.S. Pat. No. 2,906,764, issued Sep. 29, 1959, describe a process where organosilanes having at least one hydrogen and one hydrolyzable group bonded to silicon are reacted with an alkene nitrile in the presence of a diarylamine catalyst to produce preferentially β-cyanoalkylsilanes.

Jex et al., U.S. Pat. No. 2,907,784, issued Oct. 6, 1959, describe a process where organosilanes having at least one hydrogen and one hydrolyzable group bonded to silicon are reacted with an alkene nitrile in the presence of a trihydrocarbylphosphine catalyst to produce preferentially β-cyanoalkylsilanes.

Bluestein, U.S. Pat. No. 2,971,970, issued Feb. 14, 1961, describes a multiple component catalyst system useful for the production of β-cyanoalkylsilanes by the reaction of alkene nitriles with organosilanes having at least one hydrogen. The catalyst comprises a cuprous compound, a diamine, and a trialkylamine.

Rajkumar et al., Organometallics 8:549 (1989), describe a two-component catalyst effective in hydrosilation of acrylonitrile leading to the β-addition to the double bond of the acrylonitrile. The catalysts consist of cuprous oxide and tetramethylethylenediamine.

Bank, U.S. Pat. No. 5,126,468, issued Jun. 30 1992, describes a process for the preparation of hydrolyzable β-cyanoalkylsilanes. The process employs novel catalysts comprising a diamine and non-activated copper, selected inorganic copper compounds, and di-coordinate organic copper compounds.

Bank, U.S. Pat. No. 5,126,469, issued Jun. 30, 1992, describes a process for the preparation of hydrolyzable β-cyanoalkylsilanes. The process employs a catalyst comprising a diamine and supported copper or a supported copper compound.

SUMMARY OF INVENTION

The present invention is a process for the preparation of hydrolyzable β-cyanoalkylsilanes. More particularly, this invention relates to the catalytic addition of organohydrosilanes to α,β-unsaturated olefinic nitriles to form β-cyanoalkylsilanes. The present process employs a catalyst comprising a ruthenium compound. The preferred catalyst for the present process is a ruthenium compound having at least one tertiary phosphine ligand. The process is conducted at a temperature within a range of about 50° C. to 300° C.

DESCRIPTION OF INVENTION

The present invention is a process for preparation of β-cyanoalkylsilanes described by formula

  (1)

The process comprises: contacting a mixture comprising an organohydrosilane described by formula

  (2)

and an olefinic nitrile described by formula

  (3)

with an effective concentration of a ruthenium compound catalyst at a temperature within a range of about 50° C. to 300° C.; where each Y is independently selected from a group consisting of hydrogen and alkyl radicals comprising one to eight carbon atoms; each R is a radical independently selected from a group consisting of alkyls comprising one to 12 carbon atoms, cycloalkyls comprising one to eight carbon atoms, aryl, alkoxys comprising one to 12 carbon atoms, and aryloxys; X is a halogen; a=1 or 2; b=1 or 2; and a +b=2 or 3.

In carrying out the process of the present invention, the olefinic nitrile, the organohydrosilane, and the ruthenium compound catalyst are contacted in a suitable reactor. The type of reactor is not critical to the present process. However, those skilled in the art will recognize that certain metals and metal complexes such as nickel chloride amine complexes can catalyze the formation of the α-adducts of the olefinic nitriles. Therefore, it is desirable to perform the process in reactors formed from non-reactive materials.

The present process can be run as a batch, semi-batch, or continuous process. The reactor can be, for example, a continuous-stir-tank reactor. When the ruthenium compound catalyst is a heterogeneous catalyst, the reactor can be, for example, a packed-bed, a stirred-bed, a vibrating-bed, or a fluidized-bed type reactor. Preferred is when the process is run as a batch or continuous process.

A mixture comprising organohydrosilane and an olefinic nitrile as described by formula (3) is contacted with a ruthenium compound catalyst. The mixture may be formed by feeding the organohydrosilane and olefinic nitrile separately to an appropriate reactor, or alternatively the mixture may be preformed and then fed to the reactor.

Contact of the mixture comprising organohydrosilane and an olefinic nitrile with the ruthenium compound catalyst can be effected by feeding the mixture to a reactor containing the ruthenium compound catalyst. When the ruthenium compound catalyst is a homogeneous catalyst, the ruthenium compound catalyst can be premixed with one or more of the components forming the mixture comprising the organohydrosilane and an olefinic nitrile and this mixture then fed to the heated reactor. The homogeneous ruthenium compound catalyst and the mixture comprising organohydrosilane and an olefinic nitrile can be fed separately to the reactor.

Olefinic nitriles useful in the present invention are described by formula (3), where each Y is independently selected from a group consisting of hydrogen and alkyl radicals comprising one to eight carbon atoms. The substituent Y can be, for example, hydrogen, methyl, ethyl, propyl, butyl, tert-butyl, and octyl. Preferred is when each substituent Y is independently selected from a group consisting of hydrogen and methyl. The olefinic nitrile can be, for example, acrylonitrile, methacrylonitrile, crotononitrile, ethylacrylonitrile, 1-cyanobutene-1, and 2-cyanooctene-1. Preferred is when the olefinic nitrile is acrylonitrile.

The organohydrosilanes useful in the present invention are described by formula (2). The organohydrosilane can have one or two substituents R, where each R is a radical independently selected from a group consisting of alkyls comprising one to 12 carbon atoms, cycloalkyls comprising one to eight carbon atoms, aryls, alkoxys comprising one to 12 carbon atoms, and aryloxys. The substituent R can be, for example, methyl, ethyl, propyl, tert-butyl, isobutyl, dodecyl, cyclopentyl, cyclohexyl, phenyl, naphthyl, xylyl, methoxy, ethoxy, and phenyoxy. It is preferred that R be methyl. The organohydrosilane can contain one or two substituents X, where X is a halogen. Preferred is when X is a chlorine atom. The preferred organohydrosilanes are those comprising one substituent R and two substituents X and X is chlorine atoms.

The organohydrosilanes useful in the present process can have one or two hydrogen atoms substituted on the silicon atom. Preferred are those organohydrosilanes having one hydrogen atom substituted on the silicon atom.

The organohydrosilane is provided to the reactor at a molar ratio within a range of about 0.9:1 to 100:1 in relation to the olefinic nitrile. Lessor molar ratios of organohydrosilane may be used but can result in reduced yields of the desired β-cyanoalkylsilane. Greater molar ratios of organohydrosilane may be used in the process, but may result in reduced process yields due to dilution of the olefinic nitrile. It is preferred that the molar ratio of organohydrosilane to olefinic nitrile be within a range of about 1:1 to 50:1.

The mixture comprising the organohydrosilane and an olefinic nitrile is contacted with a ruthenium compound catalyst. By "ruthenium compound catalyst" it is meant those compounds of ruthenium which catalyze the beta-silation of an olefinic nitrile as described by formula (3) with an organohydrosilane as described by formula (2). Although β-cyanoalkylsilanes are the preferred product of the present invention, α-cyanoalkylsilanes may also be produced and these may also be recovered as product if desired.

Preferred is when the ruthenium compound catalyst is selected from a group consisting of ruthenium halides and ruthenium compounds having at least one tertiary phosphine ligand. Examples of ruthenium halide compounds which may be useful as catalysts in the present process include $RuCl_3$, $RuCl_3.H_2O$, $RuI_3$, and hydrated $RuBr_3$. The preferred ruthenium halide compound is $RuCl_3$. Examples of ruthenium compounds having at least one tertiary phosphine ligand, which may be useful as catalysts in the present process, include $Ru(CO)_3(PPh_3)_2$, $RuCl_2(CO)_2(PPh_3)_2$, $RuCl_2(PPh_3)_4$, $RuH_2(PPh_3)_4$, $Ru(CH_2=CH_2)(PPh_3)_3$, $RuHCl(PPh_3)_3.C_7H_8$ complex, and $RuHCl(PPh_3)_3$. The preferred ruthenium compound having at least one tertiary phosphine ligand is tris(triphenylphosphine)ruthenium(II) chloride i.e. $RuCl_2(PPh_3)_3$.

In the present process, an effective concentration of a ruthenium compound catalyst is that which increases the rate of formation of the β-cyanoalkylsilane, improves the yield of β-cyanoalkylsilane, or both, in relation to the uncatalyzed process. A preferred effective concentration of the ruthenium compound catalyst is that which provides to the process a ruthenium concentration within a range of about 0.001 to 10 mole percent based on the moles of organohydrosilane, olefinic nitrile, and catalyst present in the process. A more preferred effective concentration of the ruthenium compound catalyst is that which provides to the process a ruthenium concentration within range of about 0.05 to 1.0 mole percent.

The process is conducted at a temperature within a range of about 50° C. to 300° C. The preferred temperature for conducting the present process is within a range of about 100° C. to 170° C.

The present process is applicable for the preparation of β-cyanoalkylsilanes as exemplified by β-cyanoethylmethyldichlorosilane, β-cyanoethyldimethylchlorosilane, β-cyano(α-methyl)ethylmethyldichlorosilane, β-cyano (β-methyl)ethylmethyldiichlorosilane, β-cyano(α-ethyl)ethylmethyldichlorosilane, β-cyano(β-ethyl)ethylmethyldiichlorosilane, and β-cyanoethylphenyldichlorosilane. A preferred β-cyanoalkylsilane is β-cyanoethylmethyldichlorosilane. Those skilled in the art will recognize that α-adducts may also be a product of the present process.

The following examples are provided to illustrate the present invention. The examples are not intended to limit the scope of the present claims.

EXAMPLE 1

The ability of tris(triphenylphosphine)ruthenium(II) chloride to catalyze the reaction of methyldichlorosilane with acrylonitrile to form a β-cyanoalkylsilane was evaluated at various times, temperatures, and catalyst concentrations. The process was conducted in sealed 8 mm × 35 cm glass tubes, heat dried, and purged with argon. An amount of $RuCl_2(PPh_3)_3$ as described in Table 1 was added to a tube. Then, approximately 2.0 mL of a mixture comprising the acrylonitrile (AN) and 5.0 mole percent excess methyldichlorosilane was added to the tube. The tube was heated at a temperature and for a time as described in Table 1. The contents of the tubes were cooled and then analyzed by gas liquid chromatography (GLC) using a thermal conductivity (TC) detector. The results are presented in Table 1 as percent area under the readout curve (GLC-TC Area %) for the α-adduct and β-adduct products. The label "α-Adduct" refers to the compound MeCl₂SiCH(CH₃)CN and the label "β-Adduct" refers to the compound MeCl₂Si(CH₂)₂CN.

TABLE 1

Reaction of Methyldichlorosilane With Acrylonitrile Using RuCl₂(PPh₃)₃ as Catalyst.

| Cat. (g) | Temp. (°C.) | Time (h) | α-Adduct | β-Adduct |
|---|---|---|---|---|
| 0.0072 | 120 | 2.0 | 6.9 | 8.0 |
| 0.0049 | 120 | 19.0 | 4.1 | 18.6 |
| 0.0097 | 150 | 2.0 | 1.5 | 9.3 |
| 0.0111 | 150 | 17.0 | 3.6 | 28.3 |
| 0.0125 | 70 | 17.0 | 9.6 | 9.6 |

EXAMPLE 2

The ability of ruthenium trichloride to catalyze the reaction of methyldichlorosilane with acrylonitrile to form a β-cyanoalkylsilane was evaluated. The process was conducted in sealed glass tubes as described for Example 1. The amount of RuCl₃ added to a tube and the temperature and length of time the tube was heated is given in Table 2. At the end of the heating period the contents of the tubes were cooled and analyzed by GLC-TC as described in Example 1 and the results are presented in Table 2. The heading of Table 2 are the same as described for Table 1.

TABLE 2

Reaction of Methyldichlorosilane With Acrylonitrile Using RuCl₃ as Catalyst.

| Cat. (g) | Temp. (°C.) | Time (h) | α-Adduct | β-Adduct |
|---|---|---|---|---|
| 0.0246 | 120 | 2.0 | 2.4 | 29.5 |
| 0.0323 | 120 | 17.0 | 0.4 | 5.4 |
| 0.0298 | 150 | 2.0 | 1.8 | 23.7 |
| 0.0228 | 150 | 17.0 | 0.0 | 8.5 |

I claim:

1. A process for preparation of β-cyanoalkylsilanes described by formula

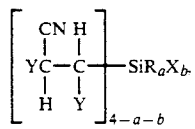

the process comprising: contacting a mixture comprising an organohydrosilane described by formula

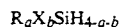

and an olefinic nitrile described by formula

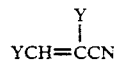

with an effective concentration of a ruthenium compound catalyst at a temperature within a range of about 50° C. to 300° C.; where each Y is independently selected from a group consisting of hydrogen and alkyl radicals comprising one to eight carbon atoms; each R is a radical independently selected from a group consisting of alkyls comprising one to 12 carbon atoms, cycloalkyls comprising one to eight carbon atoms, aryls, alkoxys comprising one to 12 carbon atoms, and aryloxys; X is a halogen; a=1 or 2; b=1 or 2; and a+b=2 or 3.

2. A process according to claim 1, where each substituent Y is independently selected from a group consisting of hydrogen and methyl.

3. A process according to claim 1, where the olefinic nitrile is selected from a group consisting of acrylonitrile, methacrylonitrile, crotononitrile, ethylacrylonitrile, 1-cyanobutene-1, and 2-cyanooctene-1.

4. A process according to claim 1, where the olefinic nitrile is acrylonitrile.

5. A process according to claim 1, where the organohydrosilane is provided to the reactor at a molar ratio within a range of about 0.9:1 to 100:1 in relation to the olefinic nitrile.

6. A process according to claim 1, where the organohydrosilane is provided to the reactor at a molar ratio within a range of about 1:1 to 50:1 in relation to the olefinic nitrile.

7. A process according to claim 1, where the ruthenium compound catalyst is selected from a group consisting of ruthenium halides and ruthenium compounds having at least one tertiary phosphine ligand.

8. A process according to claim 1, where the ruthenium compound catalyst is a ruthenium halide selected from a group consisting of RuCl₃, RuCl₃.H₂O, RuI₃, and hydrated RuBr₃.

9. A process according to claim 1, where the ruthenium compound catalyst is RuCl₃.

10. A process according to claim 1, where the ruthenium compound catalyst is a ruthenium compound having at least one tertiary phosphine ligand and is selected from a group consisting of Ru(CO)₃(PPh₃)₂, RuCl₂(CO)₂(PPh₃)₂, RuCl₂(PPh₃)₄, RuH₂(PPh₃)₄, Ru(CH₂=CH₂)(PPh₃)₃, RuHCl(PPh₃)₃.C₇H₈ complex, and RuHCl(PPh₃)₃.

11. A process according to claim 1, where the ruthenium compound catalyst is RuCl₂(PPh₃)₃.

12. A process according to claim 1, where an effective concentration of the ruthenium compound catalyst provides to the process a ruthenium concentration within a range of about 0.001 to 10 mole percent.

13. A process according to claim 1, where an effective concentration of the ruthenium compound catalyst provides to the process a ruthenium concentration within a range of about 0.05 to 1.0 mole percent.

14. A process according to claim 1, where the mixture is contacted with the catalyst at a temperature within a range of about 100° C. to 170° C.

15. A process according to claim 1, where the β-cyanoalkylsilane is β-cyanoethylmethyldichlorosilane.

16. A process according to claim 1, where the olefinic nitrile is selected from a group consisting of acrylonitrile, methacrylonitrile, crotononitrile, ethylacrylonitrile, 1-cyanobutene-1, and 2-cyanooctene-1; the organohydrosilane is provided to the reactor at a molar ratio within a range of about 1:1 to 50:1 in relation to the olefinic nitrile; the ruthenium compound catalyst is selected from a group consisting of RuCl₃ and RuCl₂(PPh₃)₃; ruthenium concentration in the mixture is within a range of about 0.05 to 1.0 mole percent; and the temperature is within a range of about 100° C. to 170° C.

17. A process according to claim 16, where the olefinic nitrile is acrylonitrile and the organohydrosilane is methyldichlorosilane.

18. A process according to claim 1, where each X is a chlorine atom.

* * * * *